United States Patent [19] [11] 4,254,054
Arndt et al. [45] Mar. 3, 1981

[54] PROCESS FOR THE MANUFACTURE OF 4-NITRO-4'-AMINO-DIPHENYLAMINE-2-SULFONIC ACID AND 2-NITRO-4'-AMINO-DIPHENYLAMINE-4-SULFONIC ACID

[75] Inventors: Otto Arndt; Wolfgang Tronich, both of Hofheim am Taunus, Fed. Rep. of Germany

[73] Assignee: Hoechst Aktiengesellschaft, Frankfurt am Main, Fed. Rep. of Germany

[21] Appl. No.: 83,852

[22] Filed: Oct. 11, 1979

[30] Foreign Application Priority Data

Oct. 13, 1978 [DE] Fed. Rep. of Germany ....... 2844610

[51] Int. Cl.$^3$ .......................................... C07C 143/56
[52] U.S. Cl. .................................................... 260/510
[58] Field of Search .......................................... 260/510

[56] References Cited

U.S. PATENT DOCUMENTS

| | | | |
|---|---|---|---|
| 536,431 | 0/1895 | Kahn et al. | 260/510 |
| 647,237 | 0/1900 | Schmidt | 260/510 |
| 800,735 | 0/1905 | Geldermann | 260/510 |
| 2,022,889 | 0/1935 | Lauer et al. | 260/510 |

Primary Examiner—Nicky Chan
Attorney, Agent, or Firm—Curtis, Morris & Safford

[57] ABSTRACT

4-Nitro-4'-amino-diphenylamine-2-sulfonic acid, 2-nitro-4'-amino-diphenylamine-4-sulfonic acid and their sodium salts are obtained in good yield and high purity by condensing 6- or 4-chloro-3-nitro-benzene sulfonic acid and 1,4-phenylene diamine in a saturated aqueous sodium chloride solution. The products and their desulfonation derivatives are dye precursors.

10 Claims, No Drawings

PROCESS FOR THE MANUFACTURE OF 4-NITRO-4'-AMINO-DIPHENYLAMINE-2-SULFONIC ACID AND 2-NITRO-4'-AMINO-DIPHENYLAMINE-4-SULFONIC ACID

4-Nitro-4'-amino-diphenylamine-2-sulfonic acid, 4,4'-diamino-diphenylamine-2-sulfonic acid, obtainable therefrom by reduction, and 4,4'-diamino-diphenylamine, obtainable from the latter compound by desulfonation and the corresponding isomers in which the nitro group or the second amino group are in the 2-position and the sulfo group is bound to the 4-position are intermediates for the manufacture of dyes.

It is known to produce 4-nitro-4'-amino-diphenylamine-2-sulfonic acid by condensation of the sodium salt of 6-chloro-3-nitrobenzene-sulfonic acid with 1,4-phenylene diamine in water in the presence of acid acceptors, such as sodium hydroxide, sodium carbonate or sodium acetate, and to produce therefrom the 4,4'-diamino-diphenylamine-2-sulfonic acid by subsequent reduction of the nitro group (cf. Berichte der Deutschen Chemischen Gesellschaft, No. 41 (1908), pages 3744 to 3755, more particularly pages 3752 to 3753). In this reference the splitting off of the sulfo group by means of sulfuric acid has also been described.

It has been found, however, that under the indicated condensation conditions the condensation product of 2 mols of 6- or 4-chloro-3-nitrobenzene-sulfonic acid with 1 mol of 1,4-phenylene diamine is formed as by-product which is then converted into the corresponding diamine by reduction. This diamine obtained from the biscondensation product and the decomposition products of the biscondensation product constitute disturbing impurities in the desired diamine so that an additional working up stage is required for separating the by products (cf. H. E. Fierz-David and L. Bangley, Grundlegende Operationen der Farbenchemie, Springer Verlag 1952, page 97).

Even if attempts are made to suppress the formation of the biscondensation product by an excess of 1,4-phenylene diamine, about 6 to 7% by weight of the biscondensation product is still formed. Moreover, it is necessary to remove from the waste water from the condensation the 1,4-phenylene diamine used in a large excess.

In the condensation hydrochloric acid is liberated which is transformed into sodium chloride by the mentioned acid acceptors. Moreover, industrial grade sodium salts of the sulfonic acids may contain sodium chloride so that the reaction medium, at least after the beginning of the condensation, can be considered a sodium chloride solution.

It has now been found, surprisingly, that the formation of the biscondensation product can be suppressed practically completely by using a saturated aqueous sodium chloride solution as the reaction medium for the condensation reaction.

It is, therefore, the object of the present invention to provide a process for the manufacture of 4-nitro-4'-amino-diphenylamine-2-sulfonic acid and 2-nitro-4'-amino-diphenylamine-4-sulfonic acid, and their sodium salts by condensation of the sodium salt of, respectively, 6- and 4-chloro-3-nitro-benzene-sulfonic acid with 1,4-phenylene diamine in an aqueous, sodium chloride containing medium, wherein this medium is a saturated sodium chloride solution. It proved particularly advantageous to use the mother liquor of a preceding condensation reaction.

Surprisingly, other alkali metal and alkaline earth metal chlorides do not show this favorable effect. Moreover, sodium sulfate has a distinctly weaker effect than sodium chloride.

By suppressing the formation of the biscondensation product in accordance with the invention a loss in yield is avoided and a product is obtained which, after reduction and optionally desulfonation, can be directly used as dye precursor. In a 4,4'-diamino-diphenylamine sulfate obtained after desulfonation according to U.S. Pat. No. 2,022,889 for example, neither the biscondensation product nor the decomposition products thereof can be detected by thin layer chromatography.

A further advantage of the process according to the invention resides in the fact that 4-nitro-4'-amino-diphenylamine-2-sulfonic acid and 2-nitro-4'-amino-diphenylamine-4-sulfonic acid are obtained in the form of their sodium salts which are sparingly soluble in saturated sodium chloride solution. In this manner a precipitation of the product with hydrochloric acid, as required according to the state of the art, can be dispensed with. This precipitation has the further disadvantage that for a subsequent catalytic reduction with nickel catalysts a neutralization is indispensible as these catalysts are sensitive to acids.

In the process of the invention the components can be used in a stoichiometric molar proportion or the 1,4-phenylene diamine is used in slight excess.

In the following, preferred embodiments of the process of the invention are described in detail.

Technical grade, moist sodium salt of, respectively, 6- and 4-chloro-3-nitro-benzenesulfonic acid, which may contain a certain amount of sodium chloride originating from their manufacturing processes are introduced at elevated temperature, preferably about 80° to 100° C., more preferably about 95° C., into the solution of 1,4-phenylene diamine, which is preferably used in an excess of about 10%, in saturated sodium chloride solution. It is sufficient to prepare the saturated sodium chloride solution from sodium chloride and water for the first batch as in the following batches suitably the mother liquor of the preceding batch is used. In this manner, the waste water is not polluted additionally.

The hydrochloric acid formed in the condensation is bound by acid acceptors which suitably form sodium chloride with the hydrochloric acid, for example sodium hydroxide, sodium carbonate or sodium hydrogen carbonate. The pH of the reaction medium is suitably maintained in the range of from 8 to 10, preferably at 9.

The sodium salt of 4-nitro-4'-amino-diphenylamine-4-sulfonic acid or 2-nitro-4'-amino-diphenylamine-4-sulfonic acid can be converted with hydrochloric acid into the sparingly soluble inner salt which can be isolated by filtration. According to a preferred embodiment the sodium salt, which is sparingly soluble in saturated sodium chloride solution, is directly isolated by filtration at a lower temperature, advantageously room temperature.

When the free sulfonic acid is precipitated with a mineral acid, preferably hydrochloric acid, it is washed with water after filtration until it is free from mineral acid and chloride. When the sodium salt is isolated it is washed with saturated sodium chloride solution.

The condensation product is obtained in such a purity that after the usual reduction, for example with iron or catalytically with hydrogen, optionally with following desulfonation, it can be directly used as dye precursor.

The following examples illustrate the invention. The parts and percentages are by weight unless otherwise stated.

EXAMPLE 1

519 parts of the sodium salt of 6-chloro-3-nitro-benzene-sulfonic acid (2 mols) are introduced into a solution of 95° C. of 240 parts of 1,4-phenylene diamine (2.22 mols) in 5,700 parts of saturated aqueous sodium chloride solution (26% NaCl). The hydrochloric acid set free in the immediately starting condensation is neutralized by adding 250 parts of 33% sodium hydroxide solution and a pH of 9 is constantly maintained. The reaction is terminated after approximately 6 hours.

When the condensation reaction is complete, the reaction mixture is adjusted to pH 1.5 at 70° C. by adding 240 parts of 30% hydrochloric acid. The precipitated free sulfonic acid is separated by filtration and washed with water until it is free from chloride. About 1,000 parts of moist product are obtained containing 620 parts of sulfonic acid. The product, moist with water, is added to 1,700 parts of water and a pH of 10 is adjusted by adding 200 parts of 33% sodium hydroxide solution, whereupon the whole is buffered to pH 7.0, for example with phosphoric acid. The mixture is transferred into a stainless steel hydrogenation autoclave containing 10 parts of a nickel catalyst (55% of nickel on kieselguhr) and the autoclave is scavenged with nitrogen. The reaction product is then reduced at 70° to 95° C. under a pressure of 40 bar hydrogen for approximately 30 minutes to one hour. The pressure of the autoclave is then released, the catalyst is separated from the reaction mixture having a pH of 8 by filtration over a pressure filter under nitrogen and the catalyst is washed with hot water. From the clarified filtrate (3,500 parts) the 4,4'-diamino-diphenylamine-sulfonic acid is precipitated at a pH of down to 5.5 with 250 parts of 30% hydrochloric acid. The precipitate is filtered off at 25° C. and washed with water.

About 700 parts of moist product are obtained which after drying gives 519 parts of 4,4'-diamino-diphenylamine-2-sulfonic acid having a purity of 98%, which corresponds to a yield of 92% of the theory, calculated on the amount of 6-chloro-3-nitrobenzene-sulfonic acid used.

The moist sulfonic acid obtained is added to 1,000 parts of about 70% sulfuric acid. Due to the water content of the reaction product the concentration of sulfuric acid drops to about 55%.

The mixture is stirred for 5 to 6 hours at 115° C., whereupon a clear black solution forms. This solution is poured while stirring into 2,000 parts of water of 50° to 60° C., whereby the sulfate of 4,4'-diamino-diphenylamine precipitates. The sulfate is filtered off at 25° C. and washed with water. About 1,200 parts of moist product are obtained containing 319 parts of 4,4'-diaminodiphenylamine, corresponding to a yield of 87% of the theory, calculated on 4,4'-diamino-diphenyl-2-sulfonic acid, or 80% of the theory, calculated on 6-chloro-3-nitrobenzene sulfonic acid. In the thin layer chromatogram no diazotizable and fluorescence-extinguishing secondary components are found.

EXAMPLE 2 (Comparative example)

The condensation is carried out as described in Example but without addition of sodium chloride, i.e. the 1,4-phenylene diamine is introduced into 4,200 parts of water. The hydrochloric acid set free in the condensation consumes 235 parts of 33% sodium hydroxide solution. The reaction product is precipitated with 315 parts of 30% hydrochloric acid (to pH 1.5). The catalytic reduction is carried out as in Example 1. After drying, 490 parts of 4,4'-diamino-diphenylamine-2-sulfonic acid are obtained having a content of biscondensation product of 7 to 8%.

The sulfonic acid group is split off under the conditions of Example 1. The thin layer chromatogram indicates a strong contamination by the biscondensation product.

EXAMPLE 3

The condensation is carried out as described in Example 1. However, when the condensation is terminated no hydrochloric acid is added, but the sparingly soluble sodium salt of 4-nitro-4'-amino-diphenylamine-2-sulfonic acid is isolated at 25° C.

The product is washed with 1,200 parts of saturated sodium chloride solution. About 900 parts of a moist product are obtained with 680 parts of dry substance having a content of pure compound of 596 parts. The product moist with water is added to 1,800 parts of water. The thin suspension obtained has a pH of 8.5 to 9 which is buffered to pH 7.0, for example with phosphoric acid.

4,4'-diamino-diphenylamine-2-sulfonic acid is then obtained by catalytic hydrogenation under the conditions of Example 1. After isolation about 600 parts of moist product are obtained which, after drying, give 500 parts of 4,4'-diamino-diphenylamine-2-sulfonic acid having a purity of 98%, which corresponds to a yield of 88% of the theory, calculated on 6-chloro-3-nitro-benzene sulfonic acid. The 4,4'-diamino-diphenylamine sulfate prepared therefrom by splitting off the sulfo group has the same quality as the product of Example 1.

EXAMPLE 4

The condensation is carried out as described in Example 1, using, instead of 5,700 parts of saturated aqueous sodium chloride solution, 5,800 parts (about 75%) of the mother liquor of a previous batch, for example the mother liquor of Example 3. The quality and yield of 4,4'-diamino-diphenylamine-2-sulfonic acid are the same as in Example 1.

EXAMPLE 5

Condensation and reduction are carried out as described in Example 1 with the exception that instead of the sodium salt of 6-chloro-3-nitrobenzene-sulfonic acid the sodium salt of 4-chloro-3-nitrobenzene-sulfonic acid is used. The condensation gives 620 parts of 2-nitro-4'-amino-diphenylamine-4-sulfonic acid.

The filtrate free from catalyst and resulting from the reduction of the above acid (5,200 parts) is adjusted to pH 8.0 with 575 parts of 30% hydrochloric acid and then 2,000 parts of sodium chloride are added. 2,4'-diamino-diphenylamine-4-sulfonic acid precipitates in the form of its hydrochloride which is filtered off at 25° C.

The product obtained does not contain any biscondensation product from 2 mols of 4-chloro-3-aminobenzenesulfonic acid and 1 mol of 1,4-phenylene diamine.

EXAMPLE 6 (Comparative Example)

The condensation is carried out as described in Example 2, that is to say without the addition of NaCl, but with the addition of the sodium salt of 4-chloro-3-nitro-benzenesulfonic acid instead of the sodium salt of 6-chloro-3-nitrobenzenesulfonic acid.

The reduction is carried out as described in Example 1 and the reaction product is isolated under the conditions of Example 5. The 2,4'-diamino-diphenylamine-4-sulfonic acid obtained in this manner contains 22 parts of the biscondensation product as defined in Example 5 (=5% of the theory, calculated on the main product).

What is claimed is:

1. In a process for production of 4-nitro-4'-amino-diphenylamine-2-sulfonic acid or a sodium salt thereof from a sodium salt of 6-chloro-3-nitro-benzene sulfonic acid or of 2-nitro-4'-amino-diphenylamine-4-sulfonic acid or a sodium salt thereof from a sodium salt of 4-chloro-3-nitro-benzene sulfonic acid, wherein the sodium salt of the benzene sulfonic acid is condensed with 1,4-phenylene diamine in the presence of a proton acceptor in an aqueous medium containing sodium chloride, the improvement which comprises condensing the benzene sulfonic acid with 1,4-phenylene diamine in a substantially saturated aqueous solution of sodium chloride.

2. A process as claimed in claim 1, wherein the saturated aqueous solution of sodium chloride is the mother liquor of a preceding condensation reaction.

3. A process as claimed in claim 1, which further comprises isolating the condensation product as a sodium salt by precipitating it from the saturated aqueous solution of sodium chloride while cooling the solution.

4. A process as claimed in claim 1, which comprises condensing at a temperature of from 80° to 100° C.

5. A process as claimed in claim 1, wherein 1,4-phenylene diamine is present in a molar excess of about 10%, based on the amount of the sodium salt of said benzene sulfonic acid.

6. A process as claimed in claim 1, wherein the proton acceptor is sodium hydroxide, sodium carbonate or sodium bicarbonate.

7. A process as claimed in claim 1, wherein the condensation is effected at a pH in the range of from 8 to 10.

8. A process as claimed in claim 1, wherein the sodium salt of said benzene sulfonic acid is dissolved in an aqueous saturated sodium chloride solution containing 1,4-phenylene diamine in a molar excess of about 10% over the stoichiometrically required amount at a temperature of from 80° to 100° C., the pH is adjusted to be in a range of from 8 to 10 and maintained in this range throughout the condensation by adding sodium hydroxide, sodium carbonate or sodium bicarbonate, after completion of the condensation the aqueous saturated solution of sodium chloride is cooled to precipitate condensation product, and precipitated product is isolated in the form of a sodium salt.

9. A process as claimed in claim 1, wherein the sodium salt of said benzene sulfonic acid is dissolved in an aqueous saturated sodium chloride solution containing 1,4-phenylene diamine in a molar excess of about 10% over the stoichiometrically required amount at a temperature of from 80° to 100° C., the pH is adjusted to be in a range of from 8 to 10 and maintained in this range throughout the condensation by adding sodium hydroxide, sodium carbonate or sodium bicarbonate, condensation product is precipitated as a free acid by adding hydrochloric acid and precipitate is isolated.

10. A process as claimed in claim 1, which further comprises isolating the condensation product, washing it with water or saturated sodium chloride solution, and, without intermediate drying, reducing the washed product in an aqueous medium to the corresponding diamino-diphenylaminosulfonic acid.

* * * * *